(12) United States Patent
Plank et al.

(10) Patent No.: US 7,001,057 B2
(45) Date of Patent: Feb. 21, 2006

(54) LIGHTING APPARATUS FOR GUIDING LIGHT ONTO A LIGHT POLYMERIZABLE PIECE TO EFFECT HARDENING THEREOF

(75) Inventors: Wolfgang Plank, Rankweil (AT); Gottfried Rohner, Altstatten (CH)

(73) Assignee: Ivoclar Vivadent A.G., Schaan (LI)

( * ) Notice: Subject to any disclaimer, the term of this patent is extended or adjusted under 35 U.S.C. 154(b) by 90 days.

(21) Appl. No.: 10/139,675

(22) Filed: May 6, 2002

(65) Prior Publication Data
US 2002/0176251 A1 Nov. 28, 2002

Related U.S. Application Data

(60) Provisional application No. 60/305,121, filed on Jul. 13, 2001.

(30) Foreign Application Priority Data
May 23, 2001 (DE) .................. 101 25 341

(51) Int. Cl.
*A61C 3/00* (2006.01)
(52) U.S. Cl. ................ 362/573; 362/572; 433/29
(58) Field of Classification Search ................ 362/800, 362/555, 572, 236, 240, 573; 257/98, 99, 257/100; 313/500, 512, 498, 499; 433/29
See application file for complete search history.

(56) References Cited

U.S. PATENT DOCUMENTS

| | | | |
|---|---|---|---|
| 5,283,425 A * | 2/1994 | Imamura ................. 250/208.1 |
| 5,298,768 A * | 3/1994 | Okazaki et al. ............... 257/81 |
| 5,498,883 A * | 3/1996 | Lebby et al. ................. 257/95 |
| 5,614,736 A * | 3/1997 | Neumann et al. ........... 257/102 |
| 5,634,711 A | 6/1997 | Kennedy et al. |
| 5,700,714 A * | 12/1997 | Ogihara et al. ............. 438/559 |
| 5,955,749 A * | 9/1999 | Joannopoulos et al. ....... 257/98 |
| 6,200,134 B1 * | 3/2001 | Kovac et al. ................. 433/29 |
| 6,331,111 B1 * | 12/2001 | Cao ........................... 433/29 |
| 6,476,551 B1 * | 11/2002 | Osawa et al. ............... 313/506 |
| 6,511,317 B1 * | 1/2003 | Melikechi et al. ........... 433/29 |
| 6,545,359 B1 * | 4/2003 | Ohtani et al. ............... 257/758 |
| 6,692,251 B1 * | 2/2004 | Logan et al. ................. 433/29 |
| 2001/0038992 A1 * | 11/2001 | Otsuka ........................ 433/29 |
| 2001/0046652 A1 * | 11/2001 | Ostler et al. ................. 433/29 |
| 2002/0017849 A1 * | 2/2002 | Nukanobu et al. .......... 313/310 |
| 2003/0004499 A1 * | 1/2003 | McDaniel ..................... 606/3 |

FOREIGN PATENT DOCUMENTS

| | | |
|---|---|---|
| DE | 3729012 A1 | 3/1989 |
| DE | 4302897 A1 | 8/1993 |
| DE | 19850834 A1 | 5/2000 |
| JP | 62-082022 U | 5/1987 |
| JP | 6070707 U | 10/1994 |
| JP | 10-165419 | 6/1998 |

(Continued)

*Primary Examiner*—Stephen Husar
*Assistant Examiner*—Hargobind S. Sawhney
(74) *Attorney, Agent, or Firm*—John C. Thompson; Alan S. Korman

(57) ABSTRACT

A lighting apparatus for dental purposes having plurality of light sources supported on semi-conductor bases, which are mounted on a substrate is provided. The lighting apparatus includes a reflective over surface encircling the light sources which reflects visible light. The lighting apparatus may be deployed in a light hardening device as a light source unit with the emitted light beams being conducted, in particular, by a prismatic body, to a light guiding conduit.

18 Claims, 9 Drawing Sheets

FOREIGN PATENT DOCUMENTS

| | | |
|---|---|---|
| JP | 2000-245747 | 9/2000 |
| JP | 2000-316874 | 11/2000 |
| JP | 2000-353406 | 12/2000 |
| WO | WO 00/13608 A1 | 3/2000 |

* cited by examiner

LIGHTING APPARATUS FOR GUIDING LIGHT ONTO A LIGHT POLYMERIZABLE PIECE TO EFFECT HARDENING THEREOF

CROSS-REFERENCE TO RELATED APPLICATIONS

This application claims foreign priority benefits under 35 U.S.C. §119(a)–(d) from German patent application ser. no. 101 25 341.9 filed May 23, 2001. In addition, this application claims the benefit under 35 U.S.C. §119(e) of U.S. provisional patent application Ser. No. 60/305,121 filed Jul. 13, 2001.

BACKGROUND OF THE INVENTION

The present invention relates to a lighting apparatus for guiding light onto a light polymerizable piece to effect the hardening thereof.

Light devices have been deployed for, among other applications, dental applications in which a light polymerizable plastic is hardened by irradiation with light. In order to achieve a high light density, energy rich light sources are typically deployed such as halogen glow lamps, xenon photoflash, or even high-tension discharge lamps. The high-tension discharge lamps have, in fact, an especially high light intensity and, thereby, a correspondingly high light density. However, the operational tension reaches at least 3.5 kV and a corresponding activation device is required so that such lamps are not suitable for deployment in the dental practice, at least insofar as hand operable devices are concerned.

Numerous attempts have been undertaken to improve the light density of the known light apparatus in order to achieve a complete hardening of the deeper lying layers in a rapid manner. A long-time known, conventional lighting apparatus with a light intensity of, for example, 50 mW/cm$^2$ produces, in fact, by a correspondingly longer light irradiation, a good surface hardening of the plastic or artificial piece which is to be polymerized. However, deeper lying layers are not at all hardened or, at most, only incompletely hardened. There arises a hardness gradient which leads to the result that the deeper lying, middle regions remain somewhat soft or that these regions are hardened completely at a time later than the complete hardening of the surface areas.

The known lighting apparatus lead to restoration results that are compromised by, or suffer from, in part, edge spalling problems. The known light hardenable plastics shrink slightly during the hardening process. With the known lighting apparatus, a complete hardening initially occurs first in the over/outer regions of the restoration piece. The thereafter following complete hardening of the deeper lying, central regions leads to contractions and, thus, to edge spalling formation.

SUMMARY OF THE INVENTION

The present invention offers a solution to the challenge of providing a lighting apparatus for dental purposes in which the tendency of the light hardenable materials to suffer edge spalling formation is reduced wherein the lighting apparatus can nonetheless be constructed in a cost favorable manner and can be flexibly deployed.

The lighting apparatus of the present invention offers initially an especially high light intensity. Through the compact serial arrangement of numerous light sources on a semi-conductor base, such as laser diodes or LED-chips, there exists an especially high intensity of the light output. In accordance with the present invention, the light hardenable material can be practically completely hardened, in a virtually instantaneous manner, in a single pass with high energy. In this manner, the hardness gradient is at least clearly reduced and there is no occurrence of the marked time delay between the complete hardening of the outer surfaces/edge regions and the complete hardening of the deeper lying middle regions of the light hardenable mass. The edge regions are, thus, not completely hardened ahead of the hardening of the middle regions, so that the shrinkage or contraction forces are not concentrated at the edge regions but, rather, are uniformly distributed. The tendency toward edge spalling formation is, thus, in accordance with the present invention, clearly reduced.

The apparatus of the present invention permits the cost favorable availability of a lighting apparatus having a high light output intensity. Through the reflective layers around the light sources, the light output is surprisingly significantly improved, even when it is produced from the front.

The provision of reflectors for the improvement of the irradiation characteristic of light sources is, indeed, long known; for example, many halogen glow lamps include an integrated reflector. Surprisingly, the reflection layer of the lighting apparatus of the present invention permits the light output to also be improved if the reflection layer which is opposed to the light output surface of the LED-chips is pushed back. In this connection, advantage is taken of the fact that, by virtue of the high light intensity, light is continuously reflected at the surface of the item being irradiated, with the reflected light thereafter again contacting the lighting apparatus and being reflected thereat, for example, in the region of the metallic reflection layer. It is particularly advantageous in this solution but is also advantageous in the realization or configuration of a hand-held light hardening apparatus, for a so-called counter cone to be provided, which lies in opposition to the conically shaped reflector of the halogen glow source. The light falling thereonto is reflected and is substantially completely reflected back toward the light sources, so that the light can be reflected thereat on the metallic reflection layers and the degree of efficiency or effectiveness of the light sources is increased.

The direct installation of the LED-chips on a metallic layer, in accordance with the present invention, permits as well an especially good heat conduction, in that the metal is an especially good heat conductor. The corresponding heat loss is amenable to being conducted away.

Preferable suitable metals, which come into consideration, include silver, titanium, platinum, and aluminum.

In an especially advantageous embodiment of the lighting apparatus of the present invention, a portion of the reflection layer is deployed as a connection conduit. In this connection, the reflection layer is formed on an electrically isolated layer as, for example, a silicon dioxide layer and the regions are electrically isolated from one another in a conventional manner by corresponding strips having no reflection layer. The metallic reflection layer is well suited for the bonding of the connections of the LED-chips to the connection conduit by wire connectors.

In a particularly favorable embodiment of the lighting apparatus of the present invention, it is provided that the reflection layers extend, as viewed outwardly from the LED-chips, at an angle toward the front and a micro reflector is formed in a surrounding manner on each chip. These micro reflectors improve the focusing of the light beams emitted from the light sources, whereby neighboring reflector side walls are, for all practical purposes, connected to one another immediately next to one another, so that they form separation walls between the LED-chips.

Preferably, a plurality of LED-chips are actuated in a row or in a serial manner. An approach of this type permits the wire connections to extend briefly over the separation walls and away therefrom. With such an approach, one can install a multitude of LED-chips per unit area in high density and wire-connect these to one another.

In a further modified embodiment of the lighting apparatus of the present invention, it is provided that the metallic reflection region lying between the LED-chips is substantially smaller than the LED-chips themselves. As reflection areas, there can be deployed one of the LED-chips with its metallic over surface or, on the other hand, a plural arrangement of the chips in a surrounding manner around the area, which then exhibits a desirably large surface. This approach offers the advantage that the focusing as a result of the tight arrangement of the chips to one another is better. However, in connection with a configuration of sunken LED-chips having a right-angled configuration of the separation walls, the installation density is particularly favorably high, if right-angled chips are used. The surface portion of the LED-chips on the surface, which is covered by a plural arrangement, can result in, for example, 60% coverage or, even, in connection with a flat reflection layer, reach 90%, whereby the multiple arrangement does not calculate in the surrounding surface.

It is particularly advantageous if the LED-chips in their plural arrangement are arranged in immediately neighboring contact to the mass which is to be completely hardened. In connection with this approach there arises for the first time the possibility to irradiate a predetermined area of the restoration piece with a selected LED-light source. This approach permits, for example, a more intensive irradiation of the middle and typically deeper lying regions of the restoration piece. The hardening then follows generally so that the central region completely hardens. A shrinking or contraction at this location of the restoration piece is, however, not critical with respect to edge spalling formation, in that, at this point in time, the edge area has not been completely hardened. This represents an especially advantageous progress in the state of the art in contrast to the heretofore known uniform hardening processes, whereby edge spalling formation is drastically reduced or is even completely avoided by use of the lighting apparatus of the present invention.

In accordance with a further, particularly advantageous embodiment of the lighting apparatus of the present invention, it is provided that a plurality of the LED-chips are provided in such a compact arrangement having a small dimensional area that, at least in connection with larger; and to this extent, especially critical restoration pieces, the light emissions are directed onto the central region. The material to be polymerized has a light distributing partitioning property, so that, in connection with the irradiation of the central area, the edge areas are also irradiated at a reduced intensity. Also, this type of deployment of the lighting apparatus of the present invention makes possible, at the least, an avoidance of the tendency towards edge spalling formation.

BRIEF DESCRIPTION OF THE DRAWINGS

Further details, advantages, and features of the present invention are disclosed in the hereinafter following description of an embodiment of the lighting apparatus taken in connection with the figures of the schematic drawings, in which.

DETAILED DESCRIPTION OF THE PREFERRED EMBODIMENT

Figure 1:
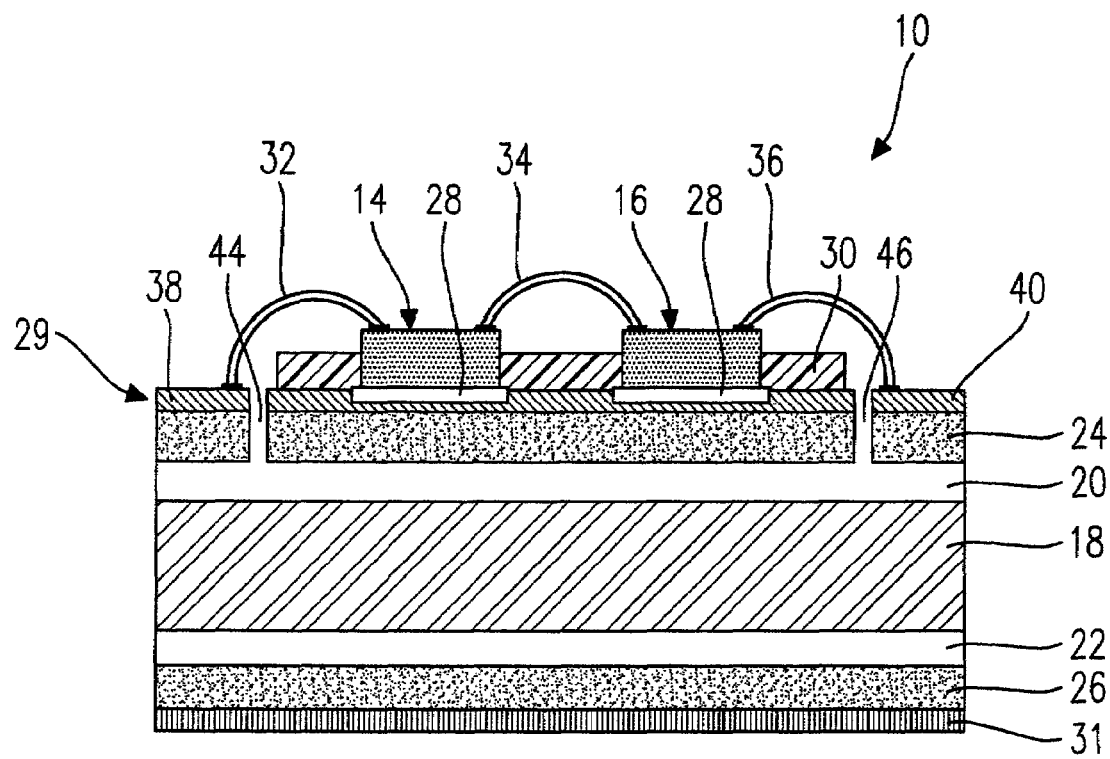
FIG. 1 is a sectional schematic view of a plural arrangement of LED-chips of one embodiment of the lighting apparatus of the present invention whereby the layer thickness is, in part, exaggeratedly emphasized.

In FIG. 1, a substantial portion of one embodiment of the lighting apparatus of the present invention, hereinafter designated as the lighting apparatus 10, is shown. The lighting apparatus comprises in this schematically shown representation two light sources 14 and 16. The light sources 14 and 16 are configured as LED-chips and include a surface of 1 mm×1 mm and a thickness of 100 micrometers, which are shown in FIG. 1 in an exaggerated manner in order to promote clarity of the represented lighting apparatus embodiment.

The light sources 14 and 16 are disposed on a substrate 18 which, in the illustrated embodiment, is a silicon wafer. The layer thickness of the wafer is 500 micrometers so that, to the extent of the representation in FIG. 1, the thickness of the wafer is shown in exaggerated manner. A wafer of this type can be produced in a conventional manner as a disk having a diameter of, for example, 10 centimeters and, in an integrated production process, numerous lighting apparatus can be produced in a serial manner in great production quantities. For example, six light sources 14, 16 can be built into a lighting apparatus 10, whereby respective pairs of the light sources are arranged in a one another adjacent manner in one direction and respective series of three light sources are arranged in a one another adjacent manner in another direction. Each lighting apparatus can comprise a surface of solely 4.3 mm×6 mm, so that a wafer can be produced with 250 lighting apparatus in a single run.

The preferred layer arrangement is hereinafter described for the production of the lighting apparatus of the present invention. On the electrically conducting wafer formed of silicon, an insulating layer 20 and 22 of silicon dioxide is formed on each of the two opposing sides of the wafer. The thickness of each layer is approximately 1 micrometer. A diffusion blocking layer 24, 26 is disposed on these layers, each diffusion blocking layer having a thickness of 2 micrometers and being comprised, for example, of tungsten-titanium.

A copper layer is disposed by sputtering on the diffusion blocking layer 26 in a thickness of 2 micrometers. In contrast, a silver layer 29 is disposed by sputtering on the diffusion blocking layer 24 having a thickness of 2 micrometers as well. The use of the diffusion blocking layers prevents silver or copper components or particles from dirtying the metallic silicon substrate, and the occurrence of disconnection locations on the affected layers.

On the silver layer 29 are formed the locations on which the LED-chip 14 or, respectively, the LED-chip 16, is to be mounted with a silver brazing 28 having a thickness of 10 micrometers and the chip is brazed or soldered.

The plastic or artificial mask 30 shown in FIG. 1 extends between the LED-chips 14 and 16 to thereby fix them in place and assure the firm seating of the arrangement. It is to be understood that the mask can be removed once a firm connection exists.

To facilitate the making available of the electrical connections, it is provided that bonding wires 32, 34, and 36 extend between the connection regions on the chips and the regions 38 and 40 of the layer 29. The layer 29 forms thereby as well a metallic reflection layer with particularly good reflection properties, in that silver is used thereat as well as on the electrical connections for the light sources 14 and 16.

To effect the electrical insulation of various regions of the reflection layer 29, surface cuts are provided. In the illustrated embodiment, two surface cuts 44, 46 are shown, whereby it is to be understood that on any suitable, desired locations, for example also between the light sources 14 and 16, corresponding surface cuts can be provided in order to make available the desired electrical insulation. The surface cuts are provided with a depth such that, at the least, the electrically conducting reflection layer 29 is clearly insulated. Preferably, the surface cuts extend in conventional manner above the silicon wafer 18. In a likewise conventional manner, each surface cut can be filled with a suitable electrically insulating substance.

A copper layer 31, as can be seen in FIG. 1, is disposed in opposition to the reflection layer 29.

Figure 2:
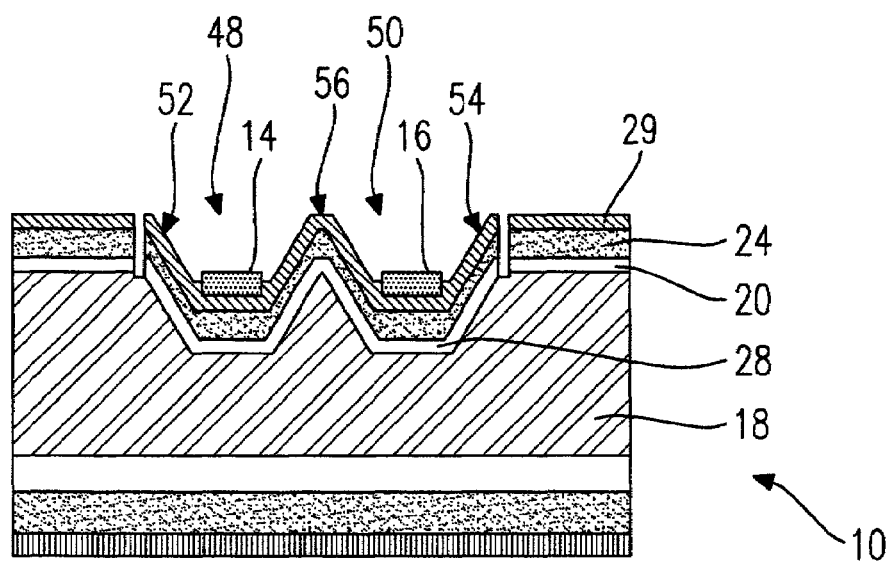
FIG. 2 is a partial sectional schematic view of another embodiment of the lighting apparatus of the present invention, whereby the layer thickness is, in part, exaggeratedly emphasized.

FIG. 2 shows another embodiment of the light apparatus of the present invention, herein designated as the light apparatus 10. The light sources 14 and 16 are arranged in a sunken manner. The same reference numerals indicate the same components as described with respect to the embodiment shown in FIG. 1. Substrate 18 includes troughs which are limited by angled walls. Such troughs can be produced, for example, by etching. Micro reflectors 48, 50 extend over the troughs in the layers shown in FIG. 1—that is, the silicon dioxide layer 20, the diffusion blocking layer 24, and the reflection layer 29. The LED-chips 14 and 16 are installed with a silver brazing surface 28 on the reflection layer 29 or, respectively, are partially sunken thereon. The walls 52, 54 extend sidewise and each form a portion of a micro reflector for each LED-chip 14 and 16.

A separate wall 56 extends between the LED-chips 14 and 16 which is, in any event, at an angle and, on its front side, extends to a peak. This configuration leads to the ladder structure which can be seen in FIGS. 5 and 6.

Figure 3:
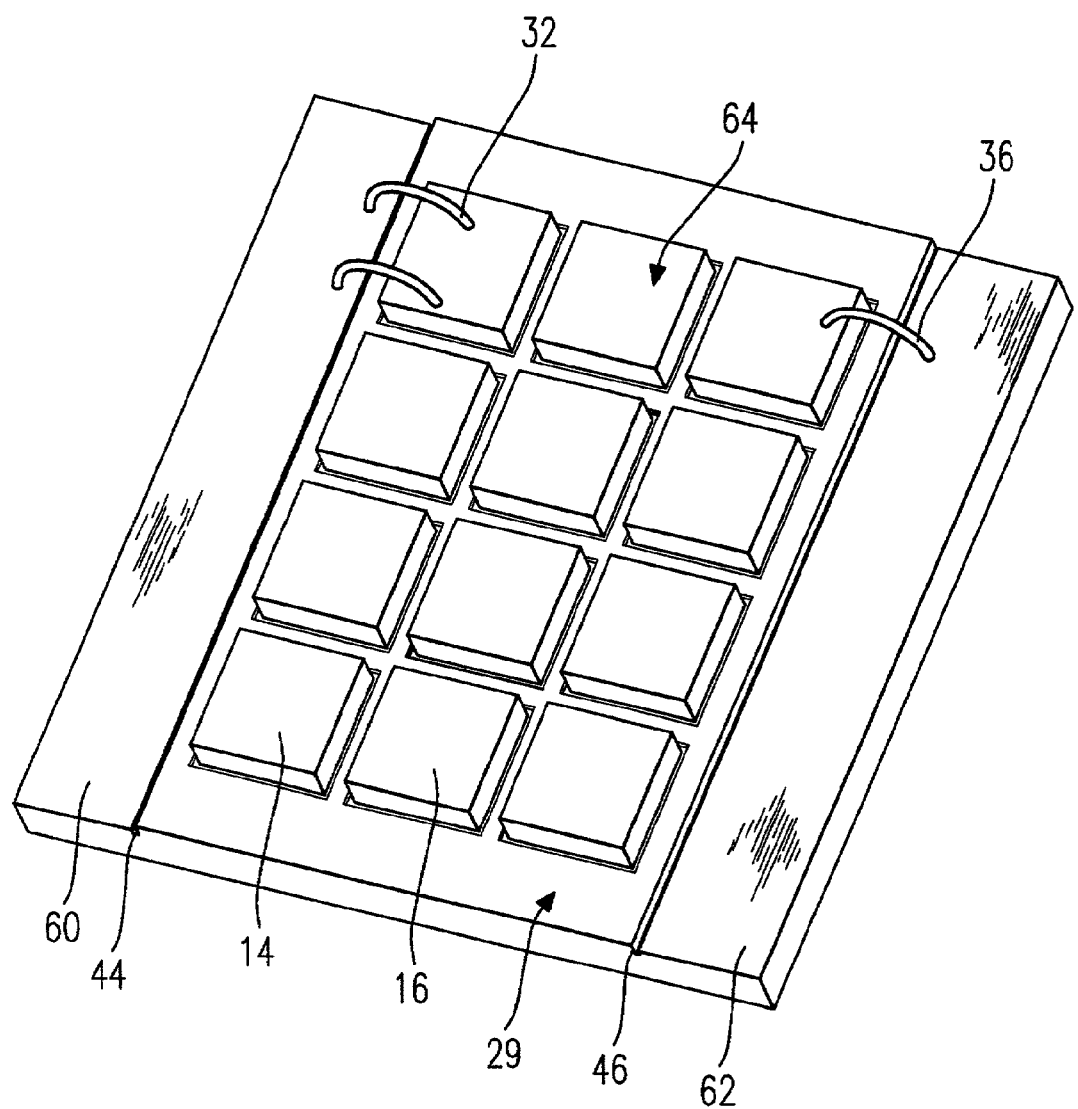
FIG. 3 is a perspective view of a further embodiment of the lighting apparatus of the present invention showing a representation of the plural arrangement showing a multiple arrangement of the LED-chips.

FIG. 3 shows the manner in which the LED-chips 14, 16 can be installed in a highly compact neighboring manner. In this configuration of the lighting apparatus of the present invention, a total of twelve LED-light sources 14, 16 are arranged in a raster. Each respective series of three light sources are connected to one another via wires as representatively shown by the wires 32 and 36 and each four of these series of the light sources are actuated in parallel. In this manner, a substantially simple energy source is provided via the two connections 60, 62.

In the embodiment of the lighting apparatus shown in FIG. 3, the reflection layer 29 extends in a substantially wide manner outside the plural arrangement 64 of the light sources 14, 16. There exists, however, relatively little space between the light sources. Also, these areas are mirrored and covered with a silver layer so that, in any event, an increase in the light efficiency or effectiveness is promoted.

Figure 4:
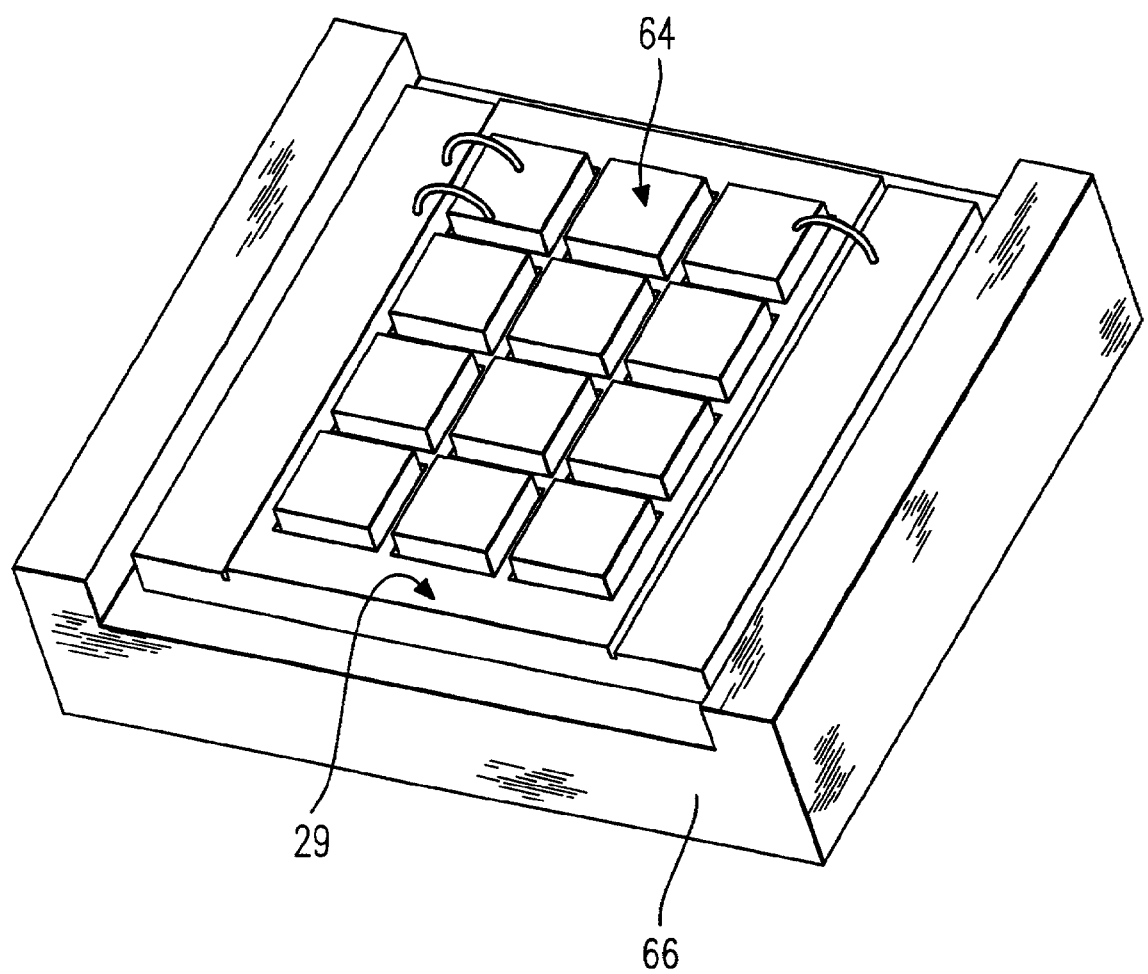
FIG. 4 is a perspective view of the further embodiment of the lighting apparatus shown in FIG. 3 and showing the installation on a base body.

As can be seen in FIG. 4, the plural arrangement of the chips 64 has been mounted. A base body 66 is provided on which the plural arrangement of the 64 light sources is supported. By means of the copper layer 31 (see FIG. 1), the resistance to heat transfer is particularly favorably at a low value and the heat conduction can be accomplished over a large surface area.

Figure 5:
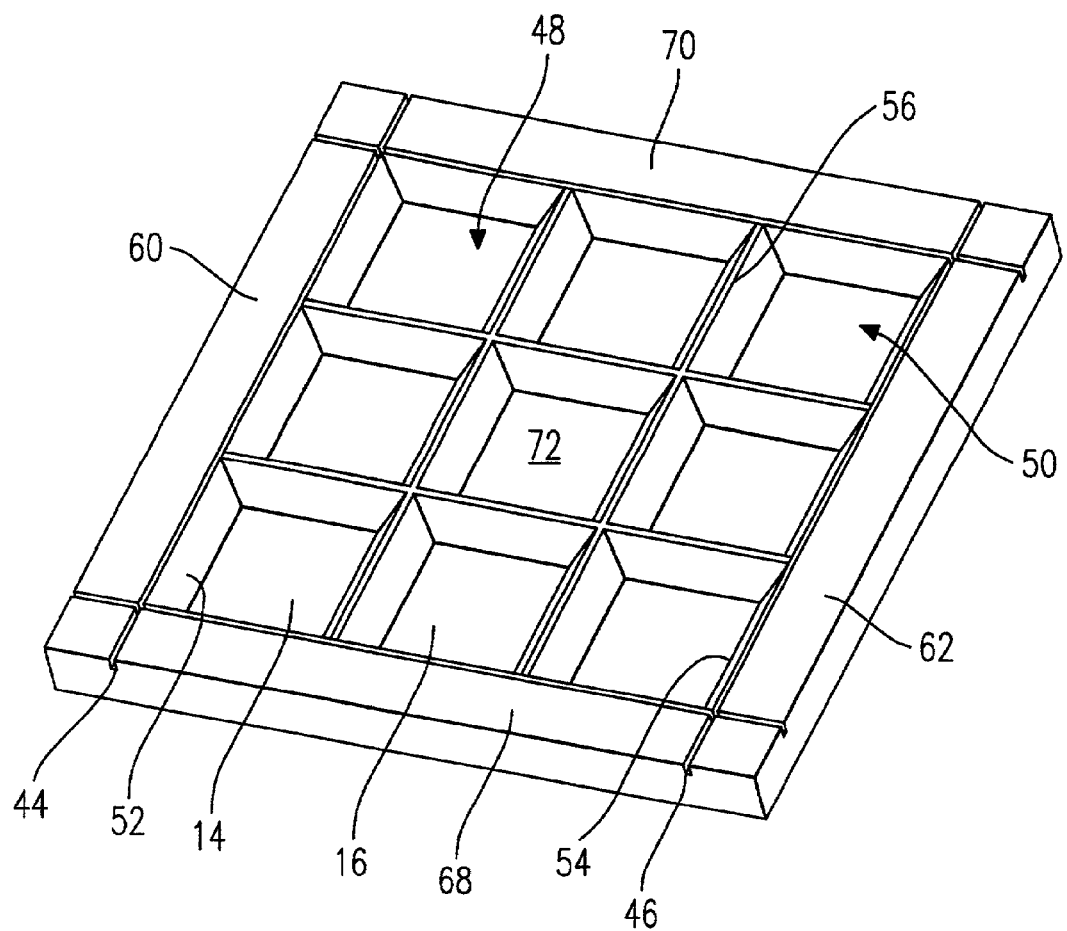
FIG. 5 is a perspective view of another embodiment of the lighting apparatus of the present invention, whereby the LED-chips are arranged in sunken manner in the micro reflectors.

As seen in FIG. 5, the separation wall 56 is V-shaped and extends to a peak and forms a raster for the receipt of nine of the LED-chips 14, 16. This embodiment makes available the two further connections 68, 70, in addition to the connections 60, 62, in another horizontal direction. The wires for the central light source 72 extend to the connections 68 and 70 so that, in this embodiment, a separate control of the central light source 72 and the otherwise available light sources 14, 16 is possible. This permits the control of the lighting apparatus in accordance with a configuration in which the lighting apparatus is deployed in a light hardening device as a light source unit and the emitted light beams are conducted, especially by a prismatic body, to a light guiding conduit.

Figure 6:
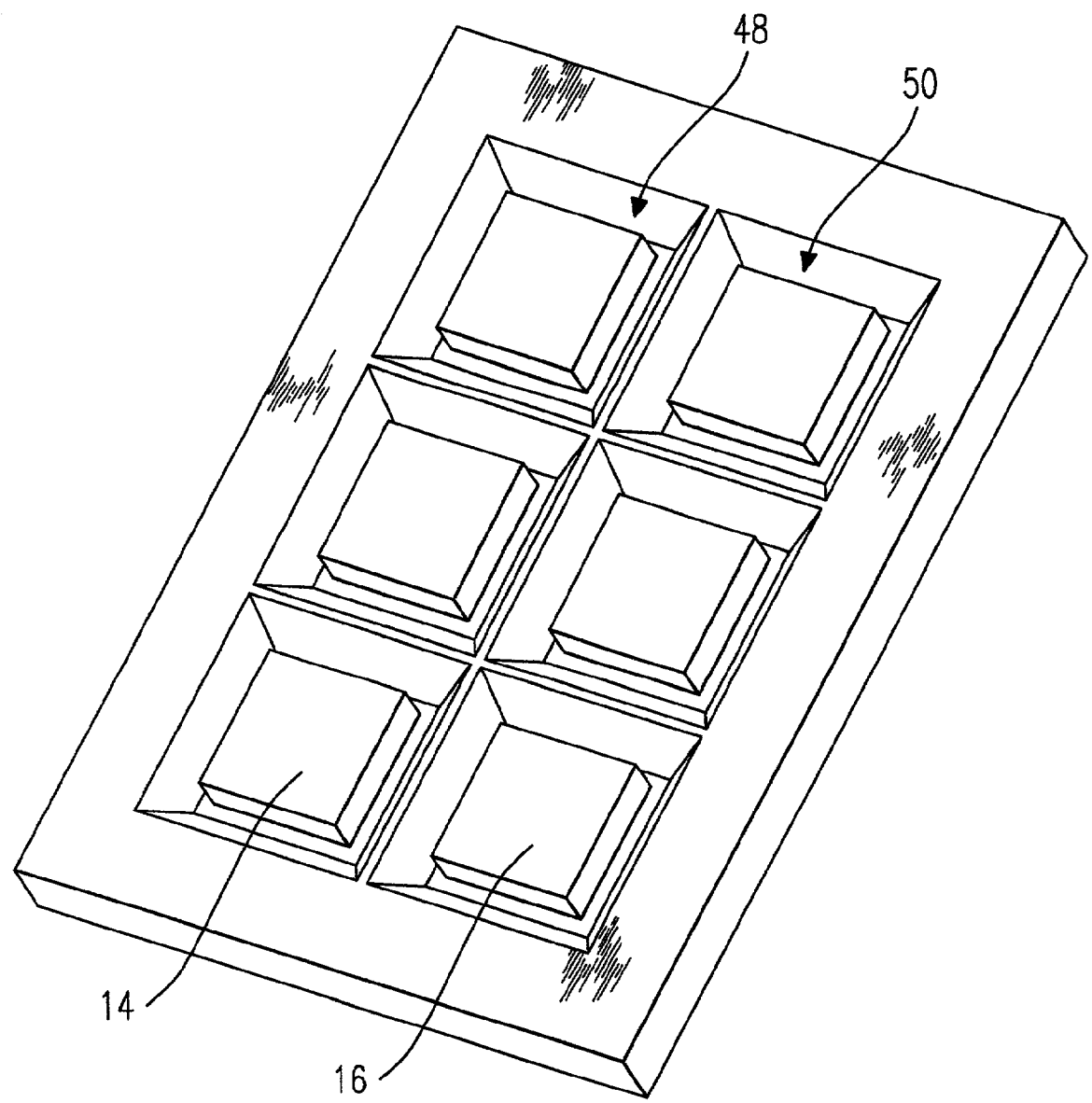
FIG. 6 is a perspective view of another embodiment of the lighting apparatus of the present invention, whereby the LED-chips are installed on the micro reflectors.

As seen in FIG. 6, the LED-chips in this embodiment of the lighting apparatus of the present invention are not arranged in a sunken manner in the micro reflectors 48 and 50 but are, instead, arranged thereon. Preferably, however, the projecting mass of the chips with respect to the base of the micro reflectors is less than the height of the micro reflectors.

Figure 7:
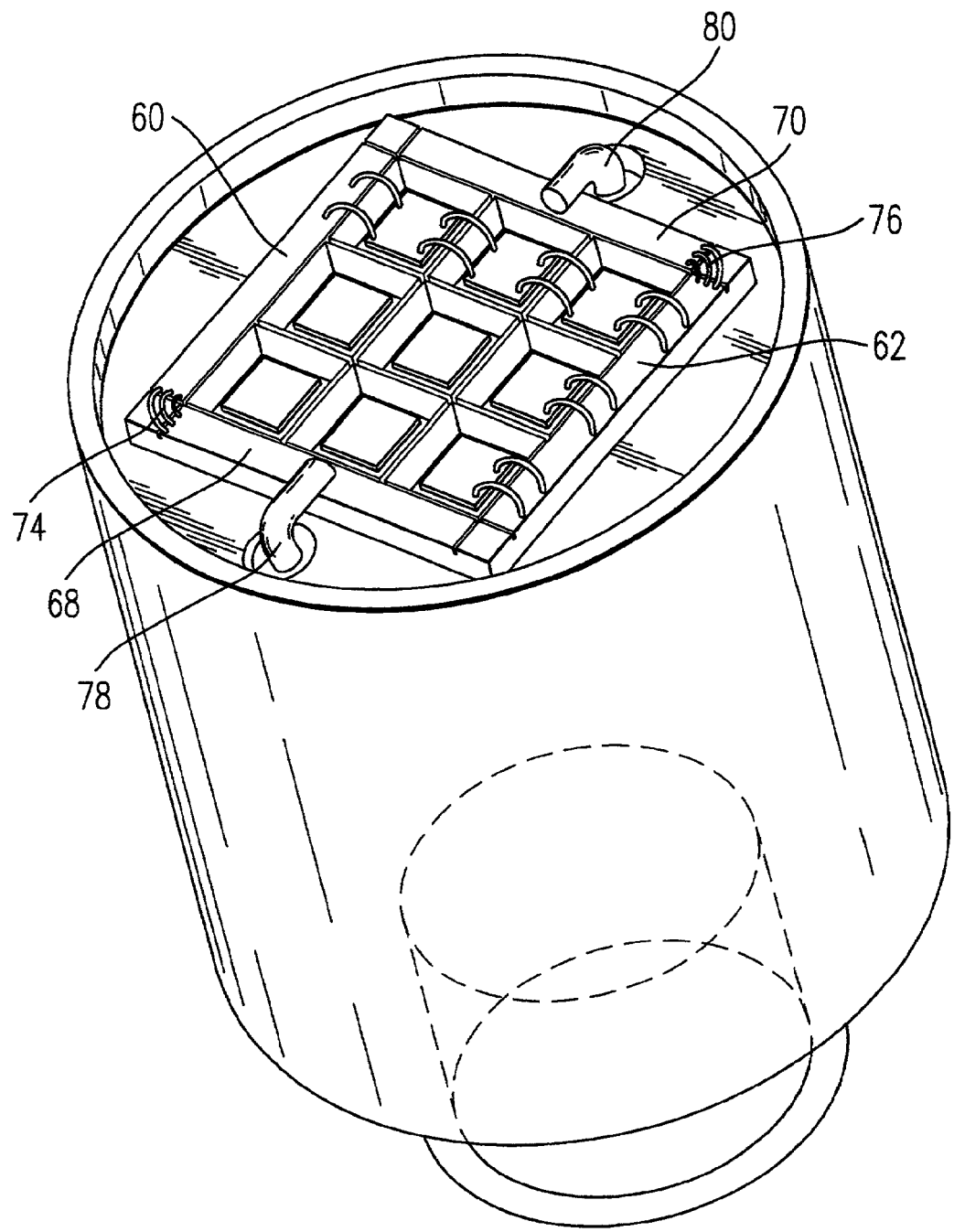
FIG. 7 is a perspective view of another embodiment of the lighting apparatus of the present invention, which is configured for the installation thereof in a hand-held light hardening device.

In FIG. 7, a further embodiment of the light apparatus of the present invention can be seen. This embodiment substantially corresponds to the embodiment shown in FIG. 5 whereby, however, no separate control of the central light source 72 is provided. Instead, in this embodiment, the connections 62 and 70, on the one hand, and the connections 60 and 68, on the other hand, are arranged in a multiple manner to be connected by the wires 74, 76. A connection wire 78 is brazed onto the connection 68 and a connection wire 80 is brazed onto the connection 70. The diameter of the copper wire provided thereat is selected such that the electrical losses are low.

Figure 8:
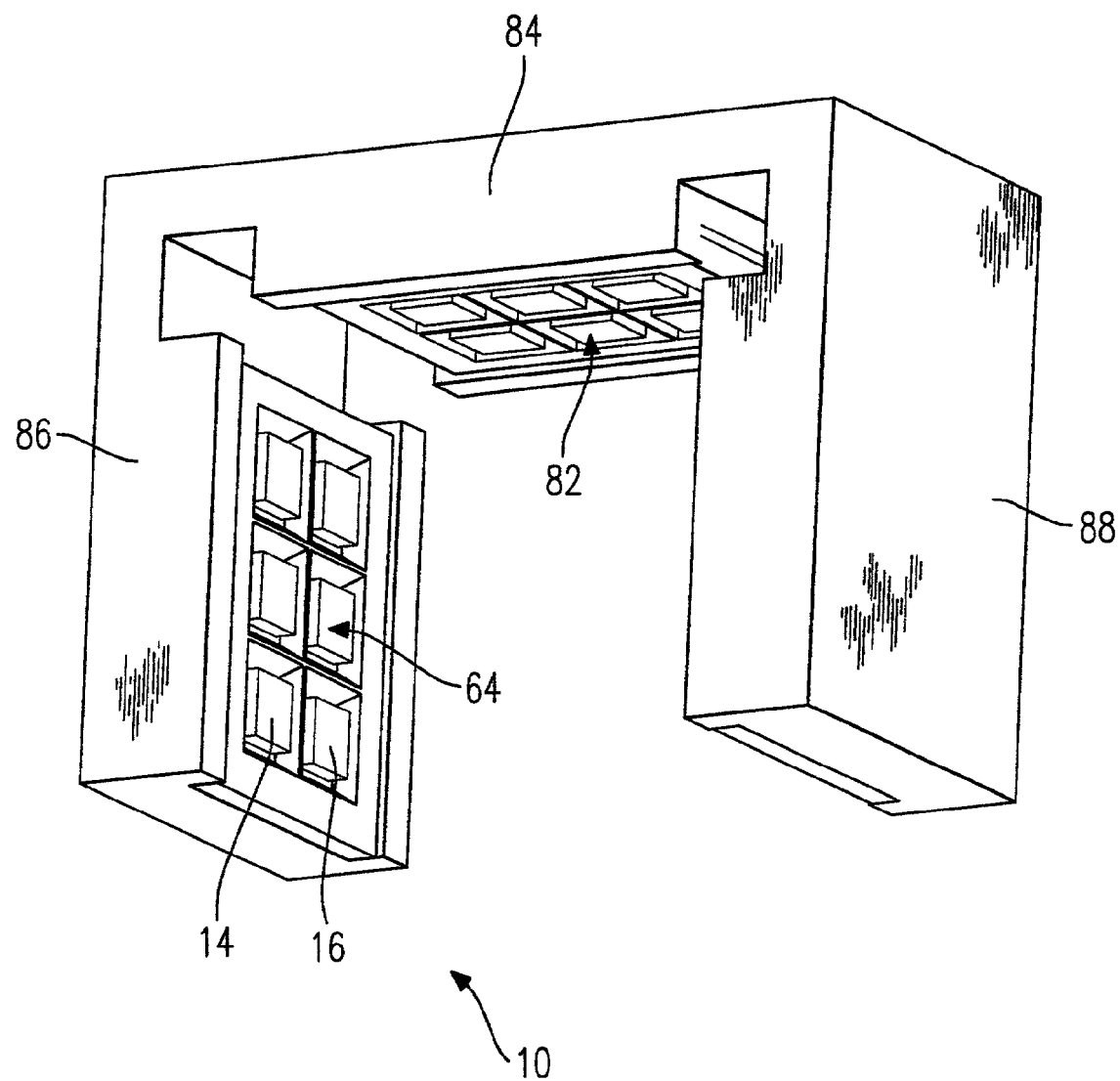
FIG. 8 is a perspective view of a further additional embodiment of the lighting apparatus of the present invention in a configuration for the complete hardening of orthodontic components.

In FIG. 8, a further additional embodiment of the lighting apparatus of the present invention is representatively shown. Several multiple arrangements 64, 82 are arranged at an angle to one another. The lighting apparatus 10 is configured in the overall shape of an inverted U and has plural arrangements 64, 82 of the light sources each disposed between its middle shank 84 and a respective one of its two side shanks 86, 88.

The interior spacing between the side shanks 86 and 88 is selected such that a molar fits therebetween. This embodiment permits the lighting apparatus 10 to operate as a form of light emitter over the tooth so that a light hardening process can be performed thereby on the tooth. Due to light irradiation from three directions, there is no longer a need for an exact post-irradiation monitoring or verification of the locations at which the light hardening has been performed so that this approach is particularly operationally reliable. This embodiment is particularly suitable for orthodontic care operations.

Figure 9:
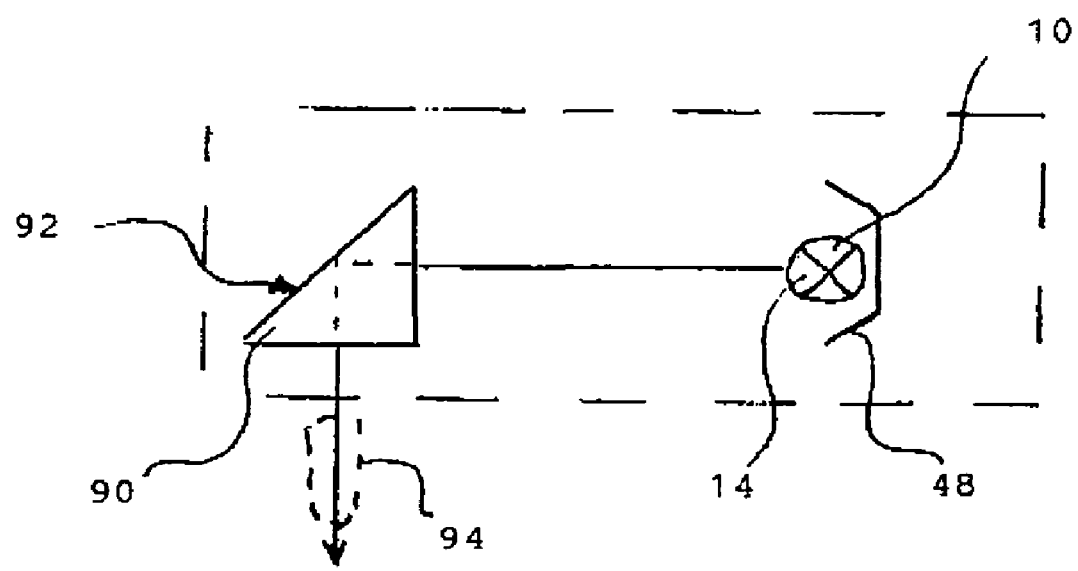
FIG. 9 shows a lighting apparatus with a light source unit which sends light via a micro-reflector to a prismatic body.

FIG. 9 shows a lighting apparatus 10 with a light source unit 14. The light unit emits light, partially directly and partially via a micro-reflector 48, toward a prismatic body 90. The prismatic body 90 has a reflective surface 93, and the light emitting from said prismatic body 90 has the desired direction. Light emitting from said prismatic body 90 is conducted to a light guiding conduit 94 shown schematically in FIG. 9.

Figure 10:
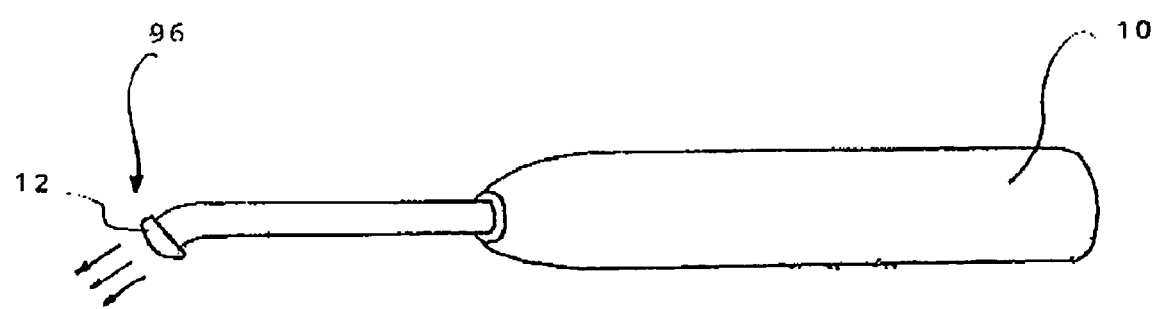
FIG. 10 shows a lighting apparatus which has a light source arranged at the head of a dental practice instrument.

FIG. 10 shows a lighting apparatus 10 which has a light source 12 arranged at the head 96 of a dental practice instrument.

The present invention is, of course, in no way restricted to the specific disclosure of the specification and drawings, but also encompasses any modifications within the scope of the appended claims.

What is claimed is:

1. A lighting apparatus, for irradiating a dental restoration piece comprising:
   a plurality of light sources supported on semi-conductor bases configured in the overall shape of an inverted U, each of which are mounted on a substrate, at least two of the light sources being disposed in an opposed relationship to one another such that they irradiate opposed sides of a dental restoration piece, and at least one further light source being disposed at right angles to said at least two light sources so that a further differing side of a dental restoration piece is irradiated; and
   a reflective over surface encircling the light sources which reflects visible light, the reflective over surface being formed by a reflection layer, which is built up upon the substrate, and wherein the reflection layer is a metallic electrically conductive layer.

2. A lighting apparatus according to claim 1, wherein the lighting apparatus is mounted on the head of a dental practice instrument and is configured for effecting the light polymerization of a light polymerizable dental restoration piece.

3. A lighting apparatus according to claim 1, wherein the light sources have dimensions within the millimeter range and, especially, are configured as LED-chips having dimensions of approximately 1 mm×1 mm and are disposable proximate to a dental restoration piece for effecting the light hardening thereof.

4. A lighting apparatus according to claim 1, wherein the reflective over surface has a coverage of more than 60%.

5. A lighting apparatus according to claim 1, wherein the reflective over surface is comprised of at least one of aluminum, silver, palladium, platinum, silicon, and ceramic.

6. A lighting apparatus according to claim 1, wherein the substrate supports the reflective over surface.

7. A lighting apparatus according to claim 1, wherein each of the light sources is surrounded by a reflection area, which is formed by a reflection layer, and the reflection areas are in neighboring disposition to one another.

8. A lighting apparatus according to claim 1, wherein LED-chips are mounted on the substrate either following the fabrication of the metallic reflection layer or are mounted onto the metallic reflection layer.

9. A lighting apparatus according to claim 8, wherein bonding wires are disposed between the LED-chips and the areas of the reflection layer and the areas of the reflection layer are wired to serve as the energy carrying means for the LED-chips.

10. A lighting apparatus according to claim 8, wherein the LED-chips are arranged in closely spaced rows and columns and connectors (60, 62, 68, and 70) are provided, and wherein connector wires (74, 76) extend between the connectors, and wherein bonding wires are disposed between the LED-chips for supplying energy to at least a portion of the chips, and the connector wires are, especially, connected by bonding.

11. A lighting apparatus according to claim 1, wherein the reflection layer is configured as a metallic layer and the substrate is a wafer of various layers including a silicon layer coated with silicon oxide, and a diffusion-blocking layer separating the silicon layer of the substrate from the metallic layer.

12. A lighting apparatus according to claim 11, wherein a silicon oxide layer is formed on the silicon wafer and the diffusion-blocking layer extends over the silicon oxide layer.

13. A lighting apparatus according to claim 1, wherein the light sources are configured as LED-chips and are disposed in a sunken manner in the substrate to form micro-reflectors, and the surface of the micro reflectors extends, as viewed from the LED-chips, toward the front at an angle.

14. A lighting apparatus according to claim 13, wherein the reflection areas are immediately bordering the LED-chips extend at an angle toward the front, especially in, an angle of approximately 56° and the LED-chips are arranged in a dense arrangement surrounded by the reflection areas.

15. A lighting apparatus according to claim 1, wherein the lighting apparatus is deployed in a light hardening device as a light source unit and the emitted light beams are conducted, especially by a prismatic body, to a light guiding conduit.

16. A lighting apparatus, for irradiating a dental restoration piece comprising:
   semi-conductor substrate configured in the overall shape of an inverted U;
   opposed light sources for hardening photopolymerizable material supported on the substrate, the opposed light sources being capable of irradiate opposed sides of a dental restoration piece, and at least one further light source being disposed at right angles to said at least two light sources so that a further differing side of a dental restoration piece is irradiated.

17. A lighting apparatus for irradiating a light polymerizable dental restoration carried by a tooth; said apparatus comprising:
   a dental practice instrument having a head;
   a semi-conductor substrate carried by the head of the dental practice instrument; and
   a plurality of light source means mounted on the semi-conductor substrate for directing light over the dental restoration cried by the tooth from three directions so that a light hardening process can be preformed thereby on differing sides of a dental restoration carried by the tooth so there is no longer a need for an exact post-irradiation monitoring or verification of the locations at which the light hardening has been performed, this approach being particularly operationally reliable, wherein at least two of the plurality of light source means are disposed in an opposed relationship to one another such that they irradiate opposed sides of the dental restoration.

18. A lighting apparatus according to claim 17, wherein at least one further light source means is disposed at right angles to said at least two light sources.

* * * * *

UNITED STATES PATENT AND TRADEMARK OFFICE
CERTIFICATE OF CORRECTION

PATENT NO. : 7,001,057 B2
DATED : February 21, 2006
INVENTOR(S) : Plank et al.

It is certified that error appears in the above-identified patent and that said Letters Patent is hereby corrected as shown below:

Column 8,
Line 63, "cried" should be -- carried --.
Line 64, "performed" should be -- preformed --.

Signed and Sealed this

Eighteenth Day of April, 2006

JON W. DUDAS
*Director of the United States Patent and Trademark Office*